United States Patent [19]

Whelan, Jr. et al.

[11] 4,142,528
[45] Mar. 6, 1979

[54] SURGICAL TUBULAR MEMBER

[76] Inventors: Joseph G. Whelan, Jr., 419 Blankenbaker La., Louisville, Ky. 40207; James P. Moss, 250 E. Liberty St., Louisville, Ky. 40202

[21] Appl. No.: 763,617

[22] Filed: Jan. 28, 1977

[51] Int. Cl.² .............................................. A61M 27/00
[52] U.S. Cl. .................................................. 128/350 R
[58] Field of Search ............................ 128/348, 350 R

[56] References Cited

U.S. PATENT DOCUMENTS

| | | | |
|---|---|---|---|
| 2,624,341 | 1/1953 | Wallace | 128/350 R |
| 2,819,719 | 1/1958 | Utley et al. | 128/350 R |
| 3,392,722 | 7/1968 | Jorgensen | 128/350 R X |
| 3,835,863 | 9/1974 | Goldberg et al. | 128/350 R |

OTHER PUBLICATIONS

Whelan — Jour. Kentucky Med. Ass., Jul. 1974.
Caprini et al. — Arch. Surg., vol. 111, Apr. 1976.

Primary Examiner—Dalton L. Truluck
Attorney, Agent, or Firm—Harry B. O'Donnell, III

[57] ABSTRACT

This invention provides a novel tubular member that can be surgically inserted into the common bile duct of a patient to perform the plural functions of, initially, providing, through its interior, a conduit for drainage of bile from inside that duct to a location outside of the body wall of the patient and, subsequently, with its exterior, promoting the growth of a fistulous tract between the outside of the body wall of the patient and the inside of the duct through which an instrument, such as a steerable basket catheter and the like, that has been non-surgically inserted into the duct via the interior of the tubular member for removal of an object, such as a retained stone and the like, contained therein, can be non-surgically withdrawn together with the object and the tubular member itself to a location outside of the body wall of the patient. Basically, the novel device that is provided by the invention comprises a hollow tubular member having the shape of a "T", with the "T" including a crossbar that can be flexed and inserted into the common bile duct through an opening that has been surgically made through the duct wall and a stem which has its junction with the crossbar constructed such that the distal end of the stem which then extends through the duct opening can be extended outwardly through an incision that has been surgically made through the body wall of the patient. The crossbar and stem each have only a single lumen through its interior, with the single lumen of the stem being fluid-connected to the single lumen of the crossbar at the junction of the stem and the crossbar. And, the stem has, along its entirety, both inside and outside diametric dimensions that are, respectively, greater than the inside and outside diametric dimensions of the crossbar.

3 Claims, 8 Drawing Figures

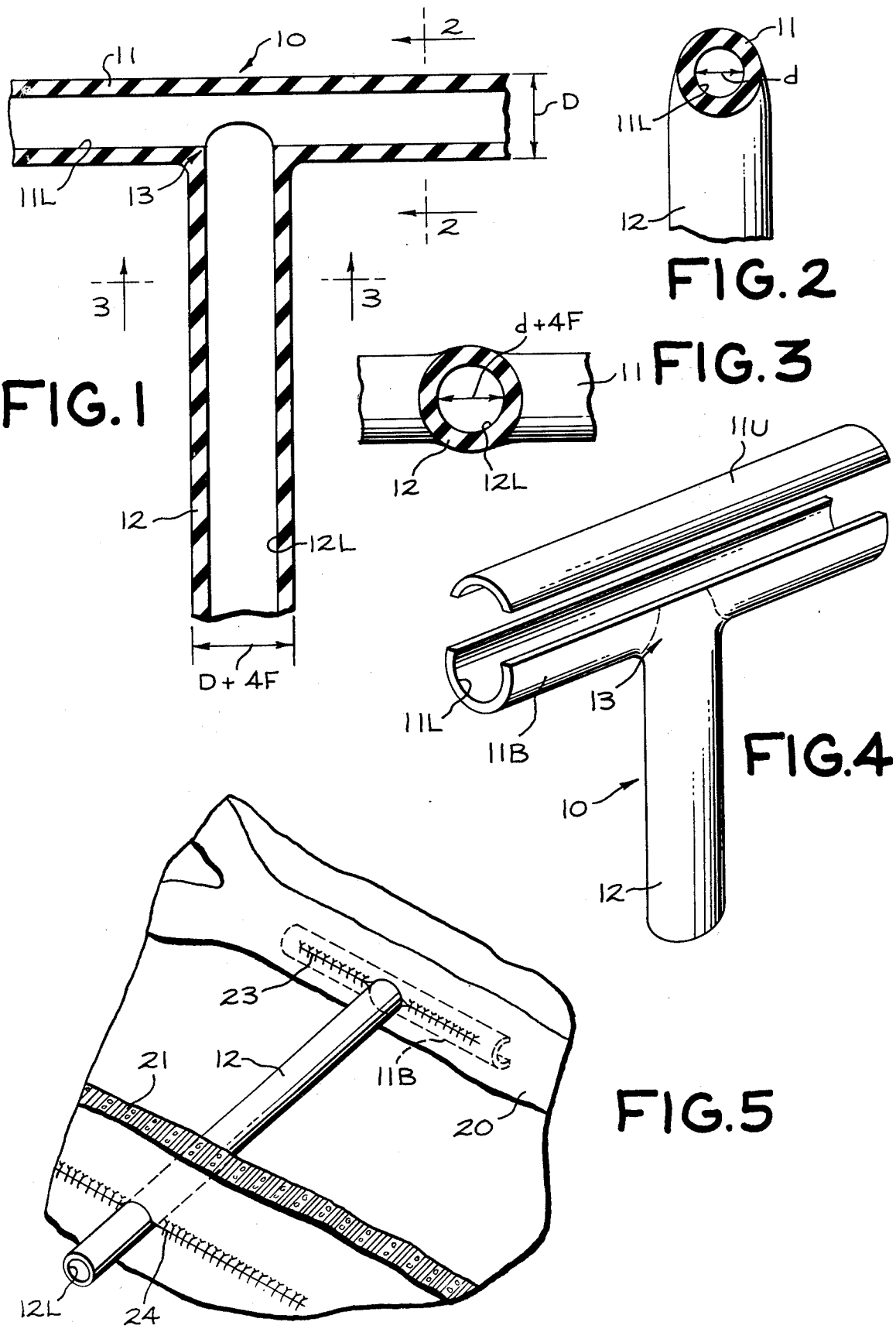

SURGICAL TUBULAR MEMBER

BACKGROUND OF THE INVENTION

This invention relates to surgical accessories and, more particularly, to a novel device comprising a hollow tubular member that can be inserted into the common bile duct of a patient during surgical procedure to perform plural beneficial functions.

The initial function performed by the novel device of the present invention is to provide, through its interior, a conduit for drainage of bile from inside the common bile duct to a location outside the body wall of the patient as is necessary during the healing process. Subsequently, however, as the healing process progresses, the novel device of the present invention performs the additional function, with its exterior, of promoting the growth of a fistulous tract between the outside of the body wall of the patient and the inside of the duct through which an instrument, such as a steerable basket catheter and the like, that has been non-surgically inserted into the duct via the interior of the tubular member for removal of an object, such as a retained stone and the like, contained therein, can be non-surgically withdrawn together with the object and the tubular member itself to a location outside of the body wall of the patient.

Once the novel device of the present invention has been withdrawn from the patient, it also provides, through the fistulous tract that has grown around the exterior of its stem, a passageway through which the aforenoted instrument can, if necessary, be non-surgically reinserted into the duct to non-surgically remove additional objects, such as additional retained stones and the like, from the duct to a location outside the body wall of the patient. And, that same fistulous tract can also provide a passageway through which yet another instrument, such as a flexible fiberoptic endoscope and the like, can be non-surgically inserted into the duct to inspect the same and, if desired, to remove biopsy tissue from the duct to a location outside the patient.

The novel device that is provided by the present invention is somewhat similar structurally to the conventional-type flexible surgical T tube drain, such as that which is shown and described in detail in U.S. Pat. No. 3,835,863, in that it also comprises a hollow tubular member having the shape of a "T", with the "T" including a crossbar that can be flexed and inserted into the common bile duct through an opening that has been surgically made through the duct wall and a stem which has its junction with the crossbar constructed such that the distal end of the stem which extends through the duct opening can be extended outwardly through an incision that has been surgically made through the body wall of the patient.

As set forth in U.S. Pat. No. 3,835,863, the aforenoted conventional-type flexible surgical T tube device can, of course, function, initially, to provide, through its interior, a conduit for drainage of bile from inside the common bile duct to a location outside of the body wall of the patient as is necessary during the healing process. And, as also has been described in recent publications, such as that by the co-inventor of the present device, Dr. Joseph G. Whelan, Jr. (Non-Operative Removal of Retained Biliary Tract Stones: Combined Percutaneous Extraction and Heparin Flushing Therapy), which appeared in the July, 1974 edition of *The Journal of the Kentucky Medical Association,* and another by Dr. Joseph A. Caprini et al (Nonoperative Extraction of Retained Common Duct Stones), which appeared in the April, 1976 edition of *Arch Surg,* such a conventional-type T tube drain or modifications thereof can also perform, as the healing process progresses, the additional function, with its exterior, of promoting the growth of a fistulous tract between the outside of the body wall of the patient and the inside of the duct through which, following removal of the conventional-type T tube drain from the patient, an instrument, such as a steerable basket catheter, can be non-surgically inserted into the duct for the non-surgical removal of objects, such as retained stones and the like, contained therein to a location outside the body wall of the patient.

As further described in the aforenoted U.S. Patent and publications, the inside and outside diametric dimensions, respectively, of both the crossbar and the stem of such a conventional-type T tube drain are the same, with, consequently, the outside diametric dimension of any instrument which can be passed through the interior of the stem, therefore, being limited to a size slightly less than the smallest inside diametric dimension of the stem and the outside diametric dimension of any object that can be non-surgically removed through the fistulous tract being limited to a dimension that is less than the smallest outside diametric dimension of the stem, which determines the smallest inside diametric dimension of the fistulous tract that is grown around it.

It is to be especially noted that attempts, following the withdrawal of such a conventional-type T tube drain from the patient, to non-surgically remove an object, such as a retained stone and the like, from the duct through the fistulous tract that has grown around the exterior of the stem of such a conventional-type T tube drain have frequently led to complications requiring emergency surgery involving re-opening of the incision through the body wall of the patient, when the largest combined outside diametric dimension of the object and the removing instrument exceeded the smallest inside diametric dimension of the fistulous tract thus grown.

As still further described in the aforenoted publications, previous efforts have also been made to enlarge the inside diametric dimension of the fistulous tract by sheathing the exterior of the stem of such a conventional-type T tube drain with a piece of tubing that has an inside diametric dimension that is similar to the outside diametric dimension of the stem and, of course, a greater outside diametric dimension, to, thus, promote the growth around the exterior of the sheathing tube piece of a fistulous tract having an enlarged inside diametric dimension when compared with that produced by the unsheathed stem, which, hence, would, in turn, permit the non-surgical withdrawal through that enlarged fistulous tract of objects having an enlarged outside diametric dimension.

While some success has been obtained in employing the just-noted practice of sheathing the stem of such a conventional-type T tube drain to promote the growth of a fistulous tract having an enlarged inside diametric dimension, there have, on the other hand, been frequent failures and other complications, typically caused by outward axial slippage of the sheath with respect to the stem in a direction away from the point at which the stem extends outwardly from the opening through the duct wall. Such slippage has, of course, produced a "bottleneck" section within the interior of the fistulous tract that has an inside diametric dimension that is substantially equal to the outside diametric dimension of the unsheathed stem, which defeats the just-described purpose of the sheathing practice. And, additional problems have been encountered with this sheathing practice, in the form of stagnation of body secretions between the surrounding sheath and the conventional-type T tube drain stem, which, in turn, can be undesirably introduced into the duct or body cavity of a patient as pus or infection, should the fistulous tract be ruptured following removal of the drain tube. Furthermore, the just-described sheathing practice does nothing whatsoever to provide the interior of the stem of the conventional-type T tube drain with any enlarged inside diametric dimension, which, in turn, would permit the insertion therethrough and into the duct of instruments having enlarged outside diametric dimensions.

However, in particular accordance with the present invention, the novel device that is provided thereby has a most-important structural difference from the aforenoted conventional-type T tube drain, in that it is constructed such that its stem has, along its entirety, both inside and outside diametric dimensions which are, respectively, greater than the inside and outside diametric dimension of its crossbar. Thus, with this just-noted novel structure, the device of the present invention provides, with the greater inside diametric dimension which extends along the entirety of the interior of its stem, a wider conduit for non-surgical insertion from a location outside of the body wall of the patient of instruments having an enlarged outside diametric dimension into the duct while, at the same time, also promoting, with the greater outside diametric dimension which also extends along the entirety of the exterior of its stem, the growth of a "bottleneck-free" fistulous tract through which objects having an enlarged outside diametric dimension can be non-surgically withdrawn from the duct to a location outside of the body wall of the patient.

Once the novel device of the present invention has been withdrawn from the patient, it also provides, through the fistulous tract that has grown around the exterior of its stem, a passageway through which the aforenoted instrument can, if necessary, be non-surgically reinserted into the duct to non-surgically remove additional objects, such as additional retained stones and the like, from the duct to a location outside the body wall of the patient. And, that same fistulous tract can also provide a passageway through which yet another instrument, such as a flexible fiberoptic endoscope and the like, can be non-surgically inserted into the duct to inspect the same and, if desired, to remove biopsy tissue from the duct to a location outside the patient.

SUMMARY OF THE INVENTION

The present invention provides a novel tubular member that can be surgically inserted into the common bile duct of a patient to perform the plural functions of, initially, providing, through its interior, a conduit for drainage of bile from inside that duct to a location outside of the body wall of the patient and, subsequently, with its exterior, promoting the growth of a fistulous tract between the outside of the body wall of the patient and the inside of the duct through which an instrument, such as a steerable basket catheter and the like, that has been non-surgically inserted into the duct via the interior of the tubular member for removal of an object, such as a retained stone and the like, contained therein, can be non-surgically withdrawn together with the object and the tubular member itself to a location outside of the body wall of the patient.

Basically, the novel device that is provided by the invention comprises a hollow tubular member having the shape of a "T", with the "T" including a crossbar that can be flexed and inserted into the common bile duct through an opening that has been surgically made through the duct wall and a stem which has its junction with the crossbar constructed such that the distal end of the stem which then extends through the duct opening can be extended outwardly through an incision that has been surgically made through the body wall of the patient. The crossbar and stem each have only a single lumen through its interior, with the single lumen of the stem being fluid-connected to the single lumen of the crossbar at the junction of the stem and the crossbar. And, the stem has, along its entirety, both inside and outside diametric dimensions that are, respectively, greater than the inside and outside diametric dimensions of the crossbar.

Preferably, the stem of the novel T-shaped tubular member that is provided in accordance with the present invention has, along its entirety, both inside and outside diametric dimensions that are, respectively, at least four French Sizes greater than the inside and outside diametric dimensions of the crossbar thereof, and the junction of the stem with the crossbar is constructed such that the inside diametric dimension of the fistulous tract will be, along its entirety, from the opening thereto from the outside of the body wall of the patient to the opening therefrom into the inside of the duct, substantially equal to the outside diametric dimension of the stem.

BRIEF DESCRIPTION OF THE DRAWINGS

The present invention is illustrated in the accompanying drawings, wherein:

FIG. 1 is a fragmentary view in central longitudinal section through a presently preferred form of the novel hollow tubular member that is provided in accordance with the present invention;

FIG. 2 is a fragmentary sectional view taken along line 2—2 of FIG. 1;

FIG. 3 is a fragmentary sectional view taken along line 3—3 of FIG. 1;

FIG. 4 is an elevational perspective view of the hollow tubular member illustrated in FIG. 1, but showing the upper portion of the crossbar thereof removed therefrom, as by scissors or the like (not shown), prior to its surgical insertion into the common bile duct of a patient;

FIG. 5 is a fragmentary view, with portions broken away, illustrating the hollow tubular member of FIGS. 1-4 after it has been surgically inserted into the common bile duct of a patient and also showing the manner in which the distal end of its stem extends outwardly through an incision that has been surgically made through the body wall of the patient;

DETAILED DESCRIPTION

Figure 6:
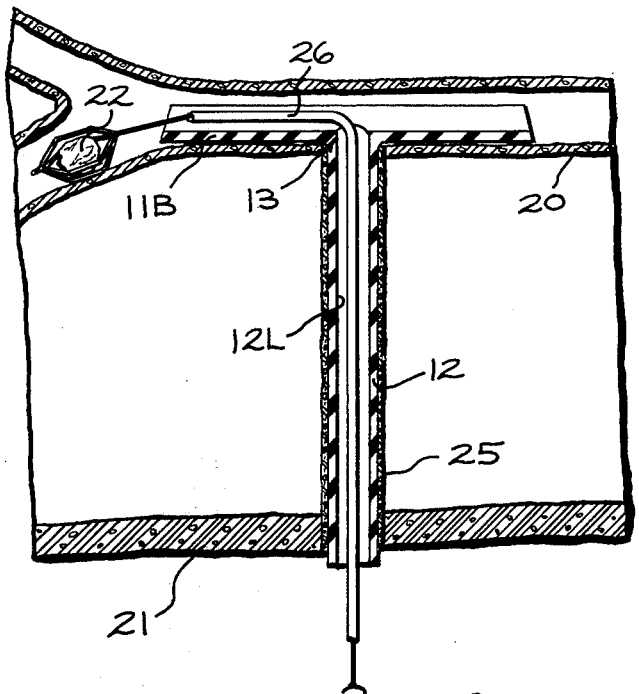
FIG. 6 is a fragmentary sectional view through the body of the patient taken along a plane passing through the longitudinal axes of the stem and the remaining lower portion of the crossbar of the novel hollow tubular member of the present invention following its aforedescribed insertion into the patient as shown in FIG. 5 and subsequent to the growth of the fistulous tract that is promoted by the exterior portion of the stem between the body wall of the patient and the interior of the common bile duct and further illustrates the manner in which an instrument, such as a steerable basket catheter and the like, can be non-surgically inserted into the duct from a location outside of the body wall of the patient through the interior of the stem.

Turning now to the drawings, and more particularly to FIGS. 1-4 thereof, there is illustrated a presently preferred form of the novel surgical accessory device 10 that is provided in accordance with the present invention. As shown, the device 10 comprises a flexible hollow tubular member having the shape of a "T", with the "T" including a crossbar 11 and a stem 12 that are integrally formed of an elastomeric material compound of a well-known variety, that is compatible with the body of the patient.

In particular accordance with the present invention and as best shown in drawing FIGS. 1-3, the crossbar of the device 10 has only a single lumen 11L through its interior and the stem 12 of the device 10 has only a single lumen 12L through its interior, with the inside diametric dimension d+4F of the single lumen 12L of the stem 12 being, along its entirety, at least four French Sizes greater than the smallest inside diametric dimension d of the single lumen 11L of the crossbar 11. And, as further illustrated, the exterior of the stem 12 of the device 10 has, along its entirety, an outside diametric dimension D+4F that is at least four French Sizes greater than the smallest outside diametric dimension D of the crossbar 11 of the device 10.

As further shown in drawing FIGS. 5-8, the novel device 10 of the present invention is particularly adapted for use as a surgical accessory in the performance of gall bladder removal surgery upon a patient to perform plural beneficial functions following the completion of such surgery. The initial function performed by the device 10 is to provide, through the interior 12L of its stem 12, a conduit for drainage of bile from inside the patient's common bile duct 20 to a location outside the body wall 21 of the patient, as is necessary during the healing process. However, perhaps more importantly, the unique construction of the novel device 10 of the present invention also enables it to subsequently perform, after the healing process has progressed, certain additional functions which facilitate the employment of instruments and techniques to non-surgically remove an object, such as a retained stone 22, from the duct 20 to a location outside the body wall 21 of the patient (FIGS. 6 and 7) and to also inspect the inside of the duct 20 and, if desired, to remove biopsy tissue from within the duct 20 (FIG. 8) to a location outside the body wall 21 of the patient.

As best shown in FIGS. 1-5, the crossbar 11 of the device 10 is inserted into the common bile duct 20 of the patient through an opening 23 that is surgically made therein during the performance of the gall bladder removal surgery. Access to the common bile duct 20 is, of course, first obtained through an incision 24 that has been made through the body wall 21 of the patient to permit the removal of the gall bladder (not shown).

Obviously, the maximum outside diametric dimension D of the crossbar 11 of the device 10 that can be employed is limited by the minimum inside diametric dimension of the common bile duct 20 into which it is to be inserted. And, as best shown in drawing FIGS. 4 and 5, it is desirable that the upper portion 11U of the crossbar 11 be removed, as by scissors or the like (not shown), before the remaining lower portion 11B of the crossbar 11 is flexed and inserted into the duct 20 via the aforenoted opening 23 that is, thereafter, closed with sutures. As further shown, the stem 12 of the device 10 has its junction 13 with the crossbar 11 constructed such that the distal end of the stem 12 then extends, after the insertion of the crossbar 11 into the opening 23 and suturing thereof, outwardly therefrom through the incision 24, which is also then closed by additional sutures, to a location outside the body wall 21 of the patient. And, as further illustrated, the fluid-connection of the single lumen 11L of the crossbar 11 and the single lumen 12L of the stem 12 of the junction 13 of the novel device 10 of the present invention is constructed such that the single lumen 12L of the stem 12, which has the larger inside diametric dimension of the two lumens 11L and 12L, extends completely through the lower wall of the crossbar 11.

With the arrangement shown in drawing FIG. 5, the novel device 10 of the present invention can, of course, initially function to provide, through the interior 12L of its stem 12, a conduit for drainage of bile from inside the common bile duct 20 to a location outside the body wall 21 of the patient as is necessary during the healing process.

Figure 7:
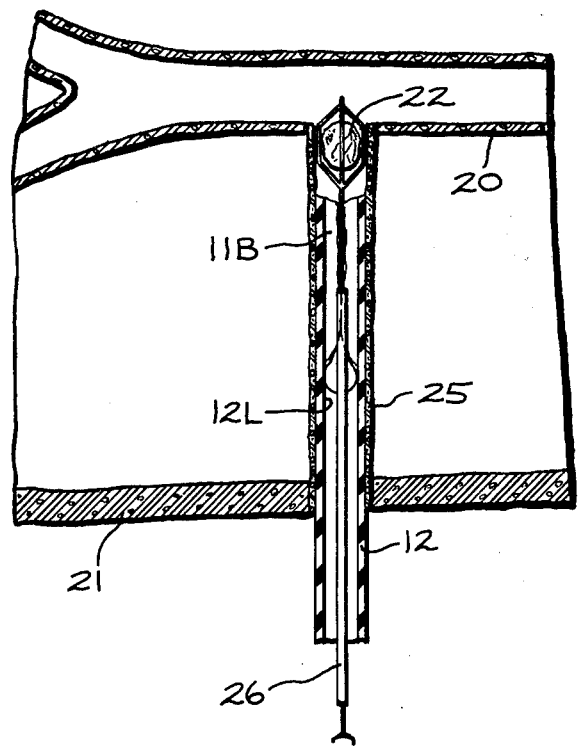
FIG. 7 is a view similar to FIG. 6 but showing the manner in which the aforenoted instrument and an object grasped thereby can be non-surgically withdrawn from the bile duct, together with the tubular member itself, through the fistulous tract to a location outside the body wall of the patient.
Figure 8:
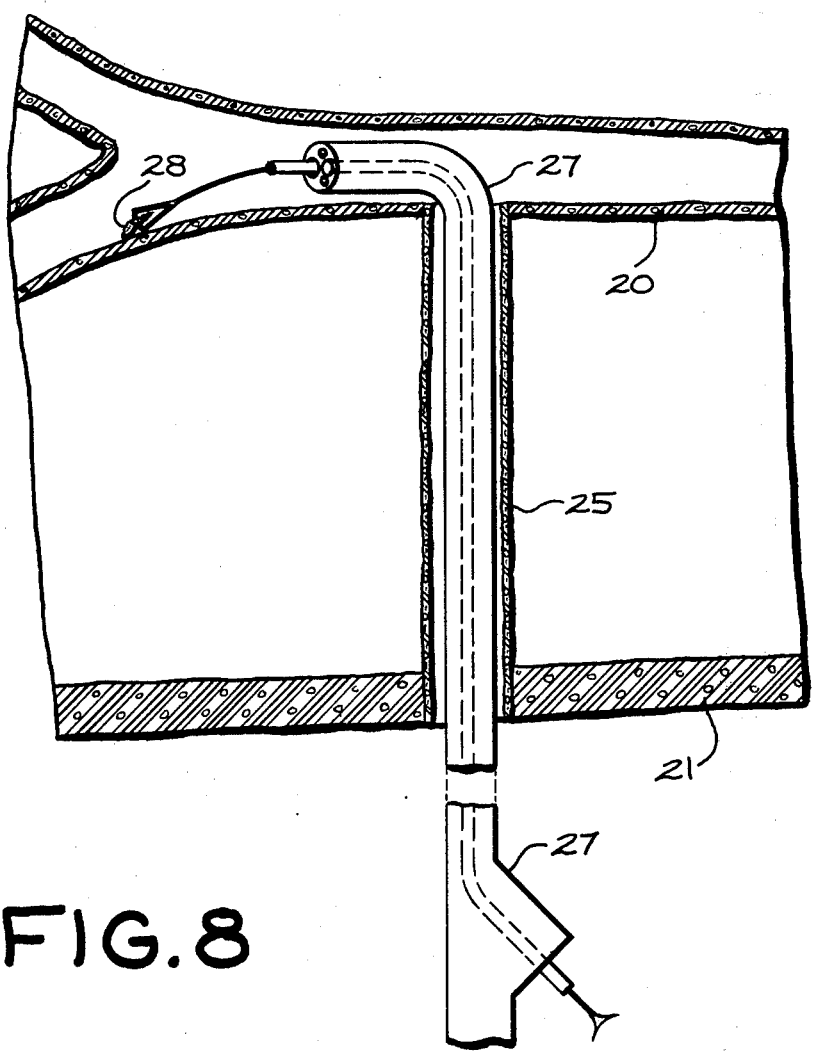
FIG. 8 is a view similar to FIGS. 6 and 7 but showing the manner in which, following the removal of the novel hollow tubular member of the present invention from the patient, yet another instrument, such as a flexible fiberoptic endoscope and the like, can be non-surgically inserted into the common bile duct via the fistulous tract to inspect the same and, if desired, to remove biopsy tissue from the duct to a location outside the body wall of the patient.

Subsequently, and perhaps more importantly, as the healing process of the patient progresses, the novel device 10 of the present invention, as best shown in drawing FIGS. 6-8, performs the additional function of promoting with the exterior of its stem 12 the growth by the patient's body function of a fistulous tract 25 completely therearound which extends between the outside of the body wall 21 to the inside of the common bile duct 20 of the patient. The desired growth of the fistulous tract 25 requires several weeks, rarely less than three and, typically, from four to six. When employing the novel device 10 of the present invention, as illustrated in the drawing FIGURES, the inside diametric dimension of the fistulous tract 25 will be, along its entirety, from the opening thereto from the outside of the body wall 21 of the patient to the opening therefrom into the inside of the common bile duct 20, substantially equal to the outside diametric dimension of the stem 12 of the device 10.

The degree of growth of the aforenoted fistulous tract 25 can, of course, be determined by fluoroscoping the patient. And, by injecting a dye into the common bile duct 20 from a location outside the body wall 21 of the patient through the conduit that is provided through the interior 12L of the stem 12 of the novel device 10 of the present invention and subsequent fluoroscoping of the patient, it can be determined prior to the withdrawal of the device 10 from the patient, whether or not any objects, such as the retained bile stone 22 illustrated in drawing FIGS. 6 and 7, need to be removed from the bile duct 20. Assuming one or more such objects is thus detected as requiring removal, the first one thereof can be non-surgically removed with an instrument, such as a steerable basket catheter 26 that can be non-surgically inserted into the duct 20 via the interior 12L of the stem 12 of the device 10 (FIG. 6) to grasp it (FIG. 6). And if, of course, the combined outside diameters of that first object 22 and the steerable basket catheter 26 do not exceed a dimension greater than the smallest inside diametric dimension of the fistulous tract 25, that first object 22 and the instrument 26 can then be non-surgically withdrawn, together with the device 10 itself, through the fistulous tract 25 from inside the common bile duct 20 to a location outside the body wall 21 of the patient (FIG. 7).

Once the novel hollow tubular device 10 of the present invention has been withdrawn from the patient, it also provides, through the fistulous tract 25 that has grown around the exterior of its stem 12L a passageway through which the aforenoted instrument 26 can, if necessary, be non-surgically re-inserted into the bile duct 20 to non-surgically remove additional objects, such as additional retained stones and the like (not shown), from the duct 20 to a location outside the body wall 21 of the patient. And, as further shown in drawing FIG. 8, that same fistulous tract 25 can, then, also provide a passageway through which yet another instrument such as a flexible fiberoptic endoscope 27 and the like, can be non-surgically inserted into the duct 20 to inspect the same and, if desired, to remove biopsy tissue 28 from the duct 20 to a location outside the body wall 21 of the patient.

It should be apparent that while there has been described herein what is presently considered to be a presently preferred embodiment of the present invention in accordance with the Patent Statutes, changes may be made in the disclosed structure without departing from the true spirit and scope of this invention. It is, therefore, intended that the appended claims shall cover such modifications and applications that may not depart from the true spirit and scope of this present invention.

What is claimed is:

1. A hollow tubular member for insertion into the common bile duct of a patient to provide a conduit from inside the duct to outside the body wall of the patient and to promote the growth of a fistulous tract between the outside of the body wall and the inside of the duct, the hollow tubular member including;
   (a) a stem and a crossbar on one end of the stem formed as one piece in a T-shape, the crossbar being flexible such that the crossbar can be flexed and inserted through a surgically formed opening in the duct wall with the stem extending through the opening in the duct and through a surgically formed opening in the body wall of the patient,
   (b) said crossbar and stem each having only a single lumen extending therethrough with the lumen in the stem being in fluid communication with the lumen in the crossbar, and
   (c) the external diameter of the stem being greater than the external diameter of the crossbar from the end of said stem which extends through the opening surgically made through the body wall of the patient to the junction of the stem with that portion of the external surface of the crossbar most proximate the stem and disposed within the duct, the remainder of the junction between the stem and crossbar being disposed within the duct and comprising a contoured external surface on the stem extending around a portion of the external surface of the crossbar such that the opening in the duct is of a diameter equal to the external diameter of the stem and the contoured portion of the stem together with the crossbar disposed within the duct are of a diameter less than the external diameter of the stem outside the duct whereby the hollow tubular member provides a conduit for drainage of bile from inside the duct to a location outside the body wall of the patient and provides a conduit for passage of an instrument so that an object, such as a retained stone, can be nonsurgically withdrawn by the instrument to a location outside the body and the fistulous tract which grows on the stem between the body wall and the duct is of an internal diameter equal to the external diameter of that portion of the stem outside the duct so that the portion of the stem within the duct and the crossbar can be readily removed through the fistulous tract and the fistulous tract and opening into the duct are sufficiently large to permit the passage of a surgical instrument into the duct after removal of the tubular member.

2. A hollow tubular member according to claim 1 wherein the diameter of the single lumen in the stem is greater than the diameter of the single lumen in the crossbar.

3. A hollow tubular member according to claim 1 wherein the inside and outside diameters of the stem are at least four French sizes greater than the respective inside and outside diameters of the crossbar.

* * * * *